United States Patent [19]
Janssens et al.

[11] 3,965,282
[45] June 22, 1976

[54] THERMOGRAPHIC RECORDING MATERIAL

[75] Inventors: Wilhelmus Janssens, Aarschot; Daniel Alois Claeys; Raymond Gerard Lemahieu, both of Mortsel; Jozef Aime Dierckx, Hove, all of Belgium

[73] Assignee: AGFA-GEVAERT N.V., Mortsel, Belgium

[22] Filed: Apr. 29, 1975

[21] Appl. No.: 572,669

Related U.S. Application Data

[62] Division of Ser. No. 428,781, Dec. 27, 1973, Pat. No. 3,911,171.

[30] Foreign Application Priority Data
Sept. 14, 1973 United Kingdom............... 43336/73
Nov. 30, 1973 United Kingdom............... 55687/73

[52] U.S. Cl.................................. 428/341; 250/317; 250/330; 282/27.5; 428/342; 428/420; 428/480; 428/537
[51] Int. Cl.².......................................... B32B 5/00
[58] Field of Search................... 427:/145, 146, 150, 427:/151, 148; 282/27.5; 428/340–342, 411, 420, 500, 522, 537, 480, 307; 250/317, 330

[56] References Cited
UNITED STATES PATENTS

| | | | |
|---|---|---|---|
| 2,770,534 | 11/1956 | Marx................................. | 117/36.2 |
| 3,751,286 | 8/1973 | Newman............................. | 428/451 |
| 3,767,449 | 10/1973 | Hayashi et al...................... | 117/36.8 |
| 3,843,383 | 10/1974 | Ishige et al......................... | 427/145 |
| 3,856,553 | 12/1974 | Hayashi et al...................... | 427/150 |
| 3,864,146 | 2/1975 | Oda et a............................. | 117/36.8 |
| 3,896,255 | 7/1975 | Kato et al........................... | 427/145 |

Primary Examiner—Thomas J. Herbert, Jr.
Assistant Examiner—Bruce H. Hess
Attorney, Agent, or Firm—William J. Daniel

[57] ABSTRACT

A thermographic recording process in which a dye is produced by bringing image-wise into reactive contact with the aid of heat a dye precursor compound and a compound with acid reaction corresponding to the following general formula:

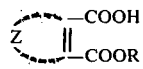

wherein :

Z represents the necessary atoms to close an unsubstituted benzene nucleus, a halogen-substituted benzene nucleus or a nitro-substituted benzene nucleus, and R represents an unsubstituted aliphatic group containing at least 4 carbon atoms, a cycloaliphatic group or an aliphatic group substituted with hydroxyl, with an etherified hydroxyl group or with an acyloxy grup.

16 Claims, No Drawings

THERMOGRAPHIC RECORDING MATERIAL

This is a division of Ser. No. 428,781 filed Dec. 27, 1973. now U.S. Pat. No. 3,911,171.

The pesent invention relates to heat-sensitive materials suited for the recording and/or reproduction of information and to recording processes wherein such materials are used.

In common thermography a heat-sensitive sheet is brought into face to face contact with a graphic original that carries an image formed of infrared radiation absorbing material. When the original is exposed to infrared radiation, the image portions thereof are heated selectively and cause by means of dye forming components development in the adjacent heat-sensitive sheet of a colour pattern corresponding to the original.

Transfer by heat of reactant materials to a receptor sheet has been described e.g. in the United Kingdom Patent Specification 973,965 and in the U.S. Pat. Nos. 2,770,534 and 3,476,578.

Heat-sensitive copy sheets in which the dye-forming compounds are present in separate layers on the same support are described e.g. in the U.S. Pat. No. 3,241,997.

Heat-sensitive copy sheets in which the dye forming reaction is based on the reaction of an acid-reacting compound with a dye precursor compound have been described in the United Kingdom Patent Specification 962,545 and the U.S. Pat. No. 2,855,266.

From the U.S. Pat. No. 3,594,208 heat-sensitive film recording materials are known in which premature reaction between a dye precursor compound and a proton-producing compound is prevented by applying the dye precursor compound in a binder layer different from the binder layer containing an acid. In practice the acid-containing coating contains cellulose nitrate as binder and is applied as an outermost layer from a solution in a volatile liquid vehicle which is a non-solvent for the vinyl chloride polymer acting as binder for the dye precursor, the layer comprising the dye precursor being applied as the first coating to the support.

From the latter Specification can be learned that organic acid reactants such as salicylic acid tend to crystallize from the cellulose nitrate binder and form light-diffusing crysalline deposits within the film. Hereby the clarity of the product is reduced and image projection e.g. with overhead projector impaired. A solution to that problem has been found by using the organic acid and a plasticizer for the cellulose nitrate in a special percent by weight ratio to the cellulose nitrate.

It has now been found that organic acids which are monoesters of aromatic orthocarboxylic acids corresponding to the following general formula:

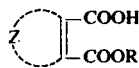

wherein:

Z represents the necessary atoms to close an aromatic nucleus or ring system including such nucleus or ring system in substituted form e.g. a benzene nucleus a halogen-substituted benzene nucleus or a nitro-substituted aromatic nucleus e.g. a nitro-substituted benzene nucleus and R represents an unsubstituted aliphatic group containing at least 4 carbon atoms or a cycloaliphatic group e.g. cyclohexyl or a straight line or branched alkyl group containing at least 4 carbon atoms or an unsaturated aliphatic group containing at least 4 carbon atoms or an aliphatic group substituted with hydroxyl, with an etherified hydroxyl group or with an acyloxy group e.g. an acetyloxy group, are particularly suited for use in thermographic recording materials in which the thermographic image formation is based on the production of a dye by the reaction of an acid with a dye precursor compound.

Said acidic mono-esters have a sufficiently high acidity to cause dye formation with dye precursors described in the Dutch Patent 6,402,618 e.g. dye progenitors of the N-bis(p-dialkylaminoaryl)methane type N-(bis(4-dimethyl-aminophenyl) methyl)pyrrolidine spiropyran compounds, Michler's hydrol and dye precursor compounds forming a methine dye as described e.g. in the United Kingdom Patent Application 59842/72 and 43337/73, which correspond to U.S. applications Ser. No. 428,688, filed Dec. 17, 1973 and Ser. No. 428,805, filed Dec. 27, 1973.

The dye precursor compounds of these Applications are preferably used for they yield highly fade-resistant dye images. Said dye precursor compounds correspond to one of the following general formulae:

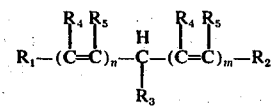

wherein:

$R_1$ represents a substituted aryl group e.g. a substituted phenyl, tolyl, xylyl, naphthyl, biphenyl, or indenyl group at least one substituent of said aryl group being an ether group $R_6$—O— in which $R_6$ represents a hydrocarbon group including a substituted hydrocarbon group, e.g. an alkyl group including a substituted alkyl group, e.g. a methyl, ethyl, propyl, hexyl, dodecyl, or octadecyl group, a cycloalkyl group including a substituted cycloalkyl group e.g. a cyclopentyl, cyclohexyl, or methylcyclohexyl group, an aralkyl group including a substituted aralkyl group e.g. a benzyl or phenethyl group, an aryl group including a substituted aryl group e.g. a phenyl group or tolyl group or a heterocyclic group including a substituted heterocyclic group e.g. an indolyl, pyrryl, thienyl, furyl, carbazolyl or indolizinyl group, $R_2$ represents a substituted aryl group e.g. a substituted phenyl, tolyl, xylyl, naphthyl, biphenyl or indenyl group, at least one substituent of said groups being an ether group $R_6$—O—, in which $R_6$ represents a hydrocarbon group including a substituted hydrocarbon group, e.g. an alkyl group including a substituted alkyl group, e.g. a methyl, ethyl, propyl, hexyl, dodecyl, or octadecyl group, a cycloalkyl group including a substituted cycloalkyl group e.g. a cyclopentyl, cyclohexyl, or methylcyclohexyl group, an aralkyl group including a substituted aralkyl group e.g. a benzyl or phenethyl group, an aryl group including a substituted aryl group e.g. a phenyl group or tolyl group or a heterocyclic group including a substituted heterocyclic group e.g. an indolyl, pyrryl, thienyl, furyl, carbazolyl, or indolizinyl group, or a

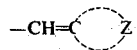

group in which Z represents the necessary atoms to close a heterocyclic nucleus including a substituted heterocyclic nucleus e.g. a nitrogen-containing heterocyclic nucleus, the indolylidene-(2) group being an example thereof, $R_3$ represents (1) a —XH or —X—$R_7$ group, in which X is oxygen or sulphur and $R_7$ is an organic group e.g. an alkyl group including a substituted alkyl group e.g. methyl, a cycloalkyl group including a substituted cycloalkyl group e.g. a cyclohexyl group, an aralkyl group including a substituted aralkyl group e.g. a benzyl group, an aryl group including a substituted aryl group e.g. a phenyl group, or an heterocyclic group including a substituted heterocyclic group,

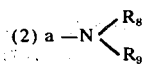

group wherein each of $R_8$ and $R_9$ (same or different) represents an alkyl group e.g. a $C_1$–$C_5$ alkyl group, a cycloalkyl group, an aralkyl group, or an aryl group or $R_8$ and $R_9$ together represent the necessary atoms to close a nitrogen-containing heterocyclic nucleus e.g. a piperidine, pyrrolidine, or morpholine nucleus, or

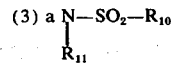

group in which $R_{10}$ represents an alkyl group including a substituted alkyl group e.g. methyl, propyl, hexyl, dodecyl, or octadecyl, or a cycloalkyl group including a substituted cycloalkyl group e.g. cyclopentyl, cyclohexyl, or methylcyclohexyl, an aralkyl group including a substituted aralkyl group e.g. benzyl or phenethyl, an aryl group including a substituted aryl group e.g. a phenyl, tolyl, xylyl, naphthyl, biphenyl or indenyl group, a heterocyclic group including a substituted heterocyclic group e.g. a pyridyl, quinolyl, benzothiazolyl, or phenothiazoyl group; the substituents being e.g. alkoxy, fluoro, chloro, bromo, dialkylamino, acylamino, or sulphamyl and in which $R_{11}$ represents hydrogen or represents a group enumerated in the definition of $R_{10}$, or $R_{11}$ and $R_{10}$ together represent a sultam group, each of $R_4$ and $R_5$ (same or different) represents hydrogen, a $C_1$–$C_5$ alkyl group, a cycloalkyl group, an aralkyl group e.g. benzyl or an aryl group e.g. a phenyl group, and each of $m$ and $n$ is 0 or 1, or

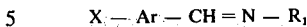

wherein:

Ar represents a bivalent aromatic nucleus e.g. phenylene, $R_1$ represents an aryl group including a substituted aryl group e.g. a phenyl, naphthyl or biphenyl group, substituents of the aryl group being e.g. an alkyl group, an alkoxy group, an alkoxycarbonyl substituted alkoxy group, a carboxyl substituted alkoxy group, an aryl sulphonyl substituted alkoxy group, a phenyl carbamoyl substituted alkoxy group, an alkyl mercapto group, an alkylamido group, or a halogen atom e.g. bromine, and X represents an a

group wherein each of $R_2$ and $R_3$ (same or different) represents an alkyl group e.g. a $C_1$–$C_5$ alkyl group, a cycloalkyl group, an aralkyl group, or an aryl group including said groups in substituted form or $R_2$ and $R_3$ together represent the necessary atoms to close a nitrogen-containing heterocyclic nucleus e.g. a piperidine, pyrrolidine, or morpholine nucleus.

The diffusion mobility of said acidic monoesters in cellulose nitrate is very low at room temperature (20°C) but is sufficiently high at copying temperature (80°–150°C) so that its rapid transfer by heat into a dye precursor containing layer is easily performed.

The acidic mono-esters that contain an aliphatic or cycloaliphatic group of at least 4 carbon atoms do not or practically do not show the unwanted crystallization in a cellulose nitrate binder and yield therefore highly transparent thermographic colour-forming film materials.

Preferred are the nitro-substituted mono-ester acids in which R represents an aliphatic or cycloaliphatic group of at least 4 carbon atoms and those in which R represents an aliphatic or cycloaliphatic group preferably of at least 4 carbon atoms and substituted with an hydroxyl group. They do not a practically do not show an unwanted cystallization in a cellulose nitrate binder and yield therefore highly transparent thermographic colour-forming film materials. The acidic mono-esters containing an R group representing an alkyl group substituted with an hydroxyl group show the highest resistance to premature dye formation.

Representatives of acidic mono-ester compounds suited for use according to the present invention are given in the following table.

| 1 | | 128 |
|---|---|---|
| | 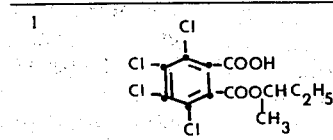 | |

-continued

| # | Structure | Property |
|---|---|---|
| 2 | 2,3,5,6-tetrachloro-benzoic acid, 2-hydroxyethyl ester (Cl₄C₆H-COOH, -COOCH₂CH₂-OH) | oil at 20°C |
| 3 | tetrachloro-benzoic acid, 3-hydroxybutyl ester (-COO-CH₂-CH₂-CH(OH)-CH₃) | resinous |
| 4 | tetrachloro-benzoic acid, 3-hydroxy-2,2-dimethylpropyl ester (-COOCH₂-C(CH₃)₂-CH₂-OH) | 125 |
| 5 | tetrachloro-benzoic acid, n-hexyl ester (-COO-(CH₂)₅-CH₃) | 48 |
| 6 | tetrachloro-benzoic acid, 2-ethylbutyl ester (-COOCH₂-CH(C₂H₅)-CH₂-CH₃) | 122 |
| 7 | tetrachloro-benzoic acid, 2-methylpentyl ester (-COOCH₂-CH(CH₃)-CH₂-CH₂-CH₃) | 104 |
| 8 | tetrachloro-benzoic acid, 2-methoxyethyl ester (-COOCH₂-CH₂-OCH₃) | 144 |
| 9 | tetrachloro-benzoic acid, cyclohexyl ester | 165 |
| 10 | tetrachloro-benzoic acid, 2-heptyl ester (-COOCH(CH₃)-(CH₂)₅-CH₃) | ±40 |
| 11 | tetrachloro-benzoic acid, n-decyl ester (-COO-(CH₂)₉-CH₃) | oil at 20°C |

-continued

| | | |
|---|---|---|
| 12 | 2,3,4,5-tetrachlorobenzoic acid, -COOCH$_2$-(CH$_2$)$_8$-CH=CH$_2$ ester | oil at 20°C |
| 13 | benzene -COOH, -COOCH(C$_2$H$_5$)(CH$_3$) | 128 |
| 14 | benzene -COOH, -CO-O-(CH$_2$)$_4$-CH$_3$, NO$_2$ | 134 |
| 15 | benzene -COOH, -COO-(CH$_2$)$_5$-CH$_3$, NO$_2$ | 172 |
| 16 | benzene -COOH, -COO-CH$_2$-CH$_2$-CH-CH$_3$ with CH$_3$, NO$_2$ | 162 |
| 17 | benzene -COOH, -CO-O-CH(CH$_3$)(CH$_2$)$_5$-CH$_3$, NO$_2$ | oil |
| 18 | benzene -COOH, -CO-O-CH$_2$-CH$_2$-O-C$_4$H$_9$, NO$_2$ | 122 |
| 19 | benzene -COOH, -COO-CH$_2$-CH$_2$-OH, NO$_2$ | 133 |
| 20 | benzene -COOH, -CO-O-CH$_2$-C(CH$_3$)$_2$-CH$_2$-OH, NO$_2$ | 170 |
| 21 | benzene -COOH, -CO-O-CH$_2$-C(C$_2$H$_5$)$_2$-CH$_2$-OH, NO$_2$ | 210 |
| 22 | benzene -COOH, -CO-O-CH$_2$-CH$_2$-O-CH$_2$CH$_2$-O-CH$_2$-CH$_2$-OH, NO$_2$ | 90–100 |

| | | |
|---|---|---|
| 23 | ![structure with NO2, COOH, CO-O-CH-CH2-O-CH2-CH-CH3, CH3, OH] | oil |
| 24 | ![structure with NO2, COO-(CH2)5-CH3, COOH] | 52 |
| 25 | ![structure with NO2, CO-O-CH2-CH2-CH(CH3)-CH3, COOH] | 76 |
| 26 | ![structure with NO2, COO-CH2-C(CH3)2-CH2-OH, COOH] | oil |
| 27 | ![O2N-phenyl-COOH, COO-(CH2)3-CH3] | oil |
| 28 | ![O2N-phenyl-COOH, COO-CH2-C(CH3)2-CH2-OH] | oil |
| 29 | ![O2N-phenyl-COOH, COO-(CH2)6-OH] | oil |

The preparation of said acidic mono-ester compounds is illustrated by the following two reaction schemes:

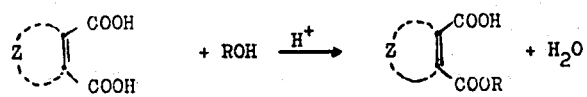

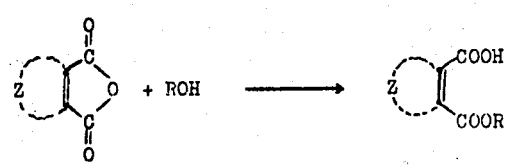

and preparation receipts A, B, C and D.

Preparation receipt A 1 mole of nitrophthalic anhydride and 3 moles of the elected alcohol, e.g. butanol, hexanol, isoamyl alcohol, are heated and refluxed on an oilbath for 3 h. The anhydride dissolves upon reaction. Thereupon the mixture is concentrated in vacuum.

Preparation receipt B 1 mole of tetrachlorophthalic acid, 3 mole of the selected alcohol and 10 ml of strong sulphuric acid refluxed for 3 h. The acid dissolves upon reaction. Thereupon the mixture is concentrated in vacuum.

Preparation receipt C 1 mole of phthalic anhydride and 3 moles of the elected alcohol, e.g. methanol, ethanol, isopropanol, iso-butanol, are heated and refluxed on an oilbath for 3 h. The anhydride dissolves upon reaction. Thereupon the pixture is concentrated under vacuum.

Preparation receipt D 1 mole of tetrachlorophthalic anhydride and 1 mole of acetic anhydride are heated for 2 h at 150°on an oilbath. The mixture is concentrated with a rotatory vacuum evaporating device and thereupon 3.5 mole of the selected alcohol are added.

For the preparation of compounds 14 to 23 of the Table particularly reference is made to J. Amer. Chem. Soc. (1937) 59, 1094.

The preparation of compound 25 is described in more details in Ber. 34, 486. Compounds 24 and 26 are prepared analogously.

The purification of the obtained mono-ester may proceed according to different embodiments A, B, C or D.

Purification embodiment A

The reaction mixture is poured into water and extracted with dichloromethane. The extract is washed several times with water and thereupon dried with anhydrous calcium chloride. The solvent is removed by evaporation under reduced pressure on a hot waterbath and the residual product is used as such.

Purification embodiment B

The reaction mixture is concentrated in a rotatory evaporating device under reduced pressure and thereupon poured into n-hexane. The obtained precipitate is sucked off and used after washing with n-hexane.

Purification embodiment C

The reaction mixture is concentrated by passing 3 times through a high vacuum evaporating device type SAMBAY (trade name) whilst heating proceeds on an oilbath at 100°C and at a pressure below 0.5 mm of mercury.

Purification embodiment D

The reaction mixture is poured into a mixture of 600 ml of methanol and 60 g of potassium hydroxide. The little precipitate formed is removed by filtration and the filtrate is concentrated in a high vacuum evaporating device at 150°C. The residue is treated with dichloromethane and an aqueous 5N solution of hydrogen chloride. The dichloromethane layer is separated and washed with water till a neutral reaction of the wash water. After drying on anhydrous calcium chloride the solvent of the extract is evaporated under reduced pressure and the obtained residue is used as such.

The acidic mono-ester compounds are suited for use in two-sheet thermographic recording systems as well as for use in an integral copy-sheet containing on a same support the acid out of direct chemical contact from the dye precursor at room temperature (20°–30°C) but in such condition that reactive contact can be effected through heating at a temperature above 60°C.

According to one embodiment of a two-sheet thermographic recording systems the dye precursor compound is applied in such a condition to or into a receptor sheet that the acid transferred from a contacting image-wise heated transfer sheet can reach this compound and react therewith to form the desired dye. The dye precursor compound is preferably applied to a receptor sheet in a binder coating, to which the acid, when heated, can be transferred from the transfer sheet.

Suitable binders for the receptor sheet are non-acidic vinyl chloride homopolymers and copolymers e.g. vinyl chloride copolymer including from 75 to 95% of vinyl chloride. Copolymers of vinyl chloride and vinyl acetate are preferred copolymers. Other copolymers of vinyl chloride e.g. with acrylonitrile are useful likewise.

Polymers and copolymers, which as a result of their molecular weight or composition become sticky on heating, have to be avoided since they prevent the easy separation of the transfer sheet from the receptor sheet.

The receptor coating or an adjacent coating may contain pigments that give an overall colour to the receptor sheet e.g. for obtaining more image contrast. For example, white pigments or coloured pigments contrasting in colour with the dye image produced may be incorporated too in the receptor sheet. Suitable pigments for that purpose are, e.g. titanium dioxide particles. The receptor coating may contain different kinds of fillers or grainy material such as silica particles that, e.g., improve the capability of being written on with pencil.

Further it may contain gloss-improving substances and anti-sticking agents, e.g. metal soaps, aluminium stearate being an example thereof.

The binder of the transfer sheet containing the acid is e.g. ethycellulose. It is, however, not absolutely necessary that the transfer sheet contains a binder; the transfer sheet may e.g. be a porous paper impregnated with the acid.

In the two sheet system good results have been obtained with an amount of dye precursor compound in a ratio of 1 part by weight to 1 to 20 parts by weight of binder in the receptor sheet. The amount of acid in the transfer sheet is preferably at least 0.1 g per sq.m.

The supports of the receptor sheet and transfer sheet are preferably flexible. Any kind of paper or resin support may be used. However, if the adherence of the coatings is too low, a suitable subbing layer or layers may be applied to the support. The support of the receptor sheet has to be transparent for visible light, when the copies obtained with the recording material have to be used for projection e.g. in an overhead projector.

In the mono-sheet system different techniques of keeping the acid reactant and the dye precursor compound out of reactive chemical contact below 60°C may be applied. For example, the reactants are kept out of direct chemical contact by enveloping at least one of the reactants in a capsule or droplet that contains a shell or envelope of a material, normally a polymeric material or wax that prevents the direct contact with the other reactant. The capsule shell or droplet envelope is ruptured or softened by heating, as a result of which the reactants come into reactive contact.

The capsules or droplets containing a first reactant may be dispersed in the paper mass of a paper sheet or in a binder or binder system containing the second reactant in dispersed or dissolved form.

The inner part of the capsule may be of organic non-water-miscible a nature and the shell or envelope may contain or consist of a hydrophilic material e.g. hydrophilic polymer or colloid that is hardened optionally. Capsules of this type have been described e.g. in the United Kingdom Patent Specifications 1,281,492, 1,276,598, and 1,034,437.

According to another embodiment the contents of the capsule are hydrophilic. For example the capsule contains water and a first reactant dissolved or dispersed therein. The capsule shell has a hydrophobic nature. The preparation of the latter type of capsules has been described in the United Kingdom Patent Specifications 1,048,696, 1,048,697, and 1,298,194 and in the published German Patent Application 2,262,676.

Preferred integral copy sheets applied in the monosheet system contain the dye precursor compound and acid reactant out of chemical reactive contact at least below 60°C in apart binder layers, the top layer having been applied from a solution in a volatile liquid, which is a non-solvent for the binder of the subjacent other layer. Premature reaction is avoided effectively when in a first layer on the support of the recording material a vinyl chloride homopolymer or copolymer binder containing the dye precursor compound and being insoluble or poorly soluble in ethanol or methanol is coated, and the acid reactant and a polymer that is higly soluble in ethanol, e.g. cellulose nitrate or polyvinyl acetate, are incorporated into a layer bonded to the first layer. The second coating preferably contains as binder medium cellulose nitrate and a copolymer of methyl methacrylate and methacrylic acid, the methacrylic acid content being preferably from 10 to 60% by weight.

If coated on a removable carrier, the very vinyl polymer film containing the dye precursor compound may serve as the backing but preferably it is permanently supported on a separate heat-resistant film, e.g. a polyester resin film, preferably a polyethylene terephthalate film. The ratio of vinyl polymer to dye precursor compound in the single sheet system may be in the range of about 20 to 3 parts by weight of dye precursor compound.

The amount of acidic mono-ester in the single sheet system material is e.g. from about 0.1 to about 0.8 parts by weight with respect to 1 part of the binder.

Particularly preferred acid reactants are the compounds 24 and 28 of the Table.

If plasticizers are used in the layer containing the acid reactant preference is given to those that do not opacify the recording material, in other words those that are compatible with the binder e.g. cellulose nitrate. The plasticizers should therefore be soluble in the same solvent as the binder. It should be essentially non-volatile in normal storage conditions. Suitable plasticizers for cellulose nitrate are "Butvar B-76" a polyvinyl butyral, polyalkylene glycol, and camphor.

The following examples illustrate the present invention. The percentages and ratios are by weight, unless otherwise indicated.

EXAMPLE 1

A polyethylene terephthalate support of a thickness of 0.10 mm was coated in the ratio of 33 ml per sq.m with the following composition:

| | |
|---|---|
| 5 % solution of copolymer of vinyl chloride and vinyl acetate (85/15) in methyl ethyl ketone | 700 ml |
| 3 % solution of a dye precursor compound having the following structural formula: | |

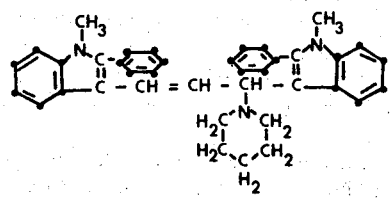

| | |
|---|---|
| in methyl ethyl ketone | 300 ml |

After drying a second layer was applied in the ratio of 70 ml per sq.m from the following composition:

| | |
|---|---|
| 5 % solution of cellulose nitrate in methanol | 500 ml |
| 10 % solution of acidic compound 16 of the Table in methanol | 70 ml |
| methanol | 430 ml |

After drying of the second layer at 50°C the resulting transparent recording material was exposed reflectographically to infrared radiation, the second layer being held in direct contact with the infrared-absorbing image markings of a printed text paper original. In accordance with the infrared absorbing image markings a blue dye has formed in the recording material.

In order to check the keepability of the recording material with regard to crystallization of the acid, the material was stored for 5 days at 35°C and 80% of relative humidity and inspected for crystallization. No trace of crystallization could be detected. In a same material prepared, however, with 55 ml of a 10% solution of phthalic acid in methanol instead of 70 ml of said 10% solution of the acidic monoester crystallization has been very pronounced already after 4 h of storage.

EXAMPLE 2

A polyethylene terephthalate support having a thickness of 0.075 mm was coated in the ratio of 30 ml per sq.m from the following composition:

| | |
|---|---|
| 5 % solution of copolymer of vinyl chloride and vinyl acetate (85/15) in methyl ethyl ketone | 800 ml |
| 3 % solution of dye precursor compound having the following structural formula: | |

$$H_3CO-\underset{OCH_3}{\underset{|}{\bigcirc}} - \underset{OCH_3}{\underset{|}{CH}} - \underset{OCH_3}{\underset{|}{\bigcirc}}-OCH_3$$

| | |
|---|---|
| in methyl ethyl ketone | 200 ml |

After drying at 50°C a second coating was applied in the ratio of 60 ml per sq.m from the following composition:

| | |
|---|---|
| 5 % solution of cellulose nitrate in methanol | 300 ml |
| 10 % solution of acidic compound 6 in methanol | 100 ml |
| methanol | 150 ml |
| isopropanol | 450 ml |

After drying of the second coating at 45°C a transparent recording material was obtained.

The recording material was exposed reflectographically to infrared radiation, the second coating being held in direct contact with the infrared-absorbing image markings of a graphic original.

A magenta image corresponding to these markings was formed.

No crystallisation could be detected after a 10 days storage of the recording material at 35°C and 80% relative humidity.

EXAMPLE 3

A polyethylene terephthalate support having a thickness of 0.075 mm was coated in the ratio of 30 ml per sq.m from the following composition:

| | |
|---|---:|
| 10 % solution of copolymer of vinyl chloride and vinyl acetate (85/15) in methyl ethyl ketone | 400 ml |
| 1 % solution of a dye precursor compound having the following structural formula: | |

$$(H_3C)_2N\text{–}\langle\rangle\text{–}CH=N\text{–}\langle\rangle\text{–}OCH_3 \quad (OCH_3)$$

| | |
|---|---:|
| in methyl ethyl ketone | 100 ml |
| 2.5 % solution of a dye precursor compound having the following structural formula: | |

[structural formula of bis-indoline dye with pentamethine chain and piperidine group]

| | |
|---|---:|
| in methyl ethyl ketone | 300 ml |
| methyl ethyl ketone | 200 ml |

After drying at 80°C a second coating was applied in the ratio of 60 ml per sq.m from the following composition:

| | |
|---|---:|
| 5 % solution of cellulose nitrate in methanol | 300 ml |
| 10 % solution of the acidic compound 13 of the Table in ethanol | 90 ml |
| methanol | 150 ml |
| isopropanol | 460 ml |

After drying of the second coating at 45°C a transparent recording material was obtained.

The recording material was exposed reflectographically to infrared radiation, the second coating being held in direct contact with the infrared-absorbing image markings of a graphic original.

A green image corresponding to those markings was form J.

EXAMPLE 4

A polyethylene terephthalate support of a thickness of 0.10 mm was coated in the ratio of 33 ml per sq.m with the following composition:

| | |
|---|---:|
| 5 % solution of copolymer of vinyl chloride and vinyl acetate (85/15) in methyl ethyl ketone | 700 ml |
| 3 % solution of a dye precursor compound having the following structural formula: | |

[structural formula of bis-indoline pentamethine dye with piperidine group]

| | |
|---|---:|
| in methyl etkyl ketone | 300 ml |

After drying a second layer was applied in the ratio of 70 ml per sq.m from the following composition:

| | |
|---|---:|
| 5 % solution of cellulose nitrate in methanol | 500 ml |
| 10 % solution of the acidic mono-ester compound 24 of the Table in methanol | 70 ml |
| methanol | 430 ml |

After drying of the second layer at 50°C the resulting transparent recording material was exposed reflectographically to infrared radiation, the second layer being held in direct contact with the infrared-absorbing image markings of a printed text paper original. In accordance with those markings a blue dye has been formed in the recording material.

In order to check the keepability of the recording material with regard to crystallization of the acid, the material was stored for 15 days at 35°C and 80% of relative humidity and inspected for crystallization. No trace of crystallization could be detected. In a same material prepared, however, with 55 ml of a 10% solution of phthalic acid in methanol instead of 70 ml of said 10% solution of the acidic mono-ester crystallization has been very pronounced already after 15 days of storage.

EXAMPLE 5

A polyethylene terephthalate support having a thickness of 0.075 mm was coated in the ratio 30 ml per sq.m from the following composition:

| | |
|---|---:|
| 5 % solution of copolymer of vinyl chloride and vinyl acetate (85/15) in methyl ethyl ketone | 800 ml |
| 3 % solution of dye precursor compound having the following structural formula: | |

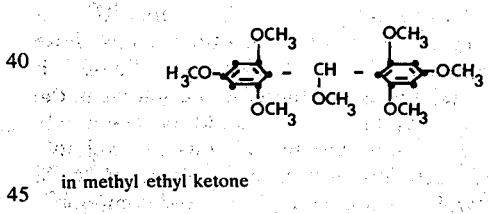

| | |
|---|---:|
| in methyl ethyl ketone | 200 ml |

After drying at 50°C a second coating was applied in the ratio of 60 ml per sq.m from the following composition:

| | |
|---|---:|
| 5 % solution of cellulose nitrate in methanol | 300 ml |
| 10 % solution of the acidic mono-ester compound 28 of the Table in methanol | 100 ml |
| methanol | 150 ml |
| isopropanol | 450 ml |

After drying of the second caoting at 45°C a transparent recording material was obtained.

The recording material was exposed reflectographically to infrared radiation, the second coating being held in direct contact with the infrared-absorbing image markings of a graphic original.

A magenta image corresponding to those markings was formed.

No crystallization could be detected after a 10 days storage of the recording material at 35°C and 80% relative humidity.

EXAMPLE 6

A polyethylene terephthalate support having a thickness of 0.075 mm was coated in the ratio of 30 ml per sq.m from the following composition:

| | |
|---|---|
| 10 % solution of copolymer of vinyl chloride and vinyl acetate (85/15) in methyl ethyl ketone | 400 ml |
| 1 % solution of a dye precursor compound having the following structural formula: | |

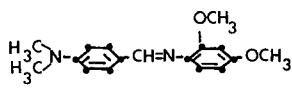

| | |
|---|---|
| in methyl ethyl ketone | 100 ml |
| 2.5 % solution of a dye precursor compound having the following structural formula: | |

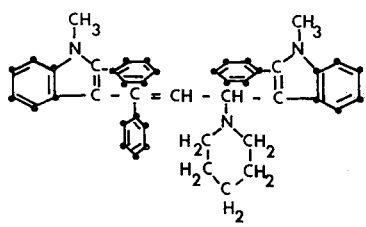

| | |
|---|---|
| in methyl ethyl ketone | 300 ml |
| methyl ethyl ketone | 200 ml |

After drying at 80°C a second coating was applied in the ratio of 60 ml per sq.m from the following composition:

| | |
|---|---|
| 5 % solution of cellulose nitrate in methanol | 300 ml |
| 10 % solution of the acidic mono-ester compound 23 of the Table in ethanol | 90 ml |
| methanol | 150 ml |
| isopropanol | 460 ml |

After drying of the second coating at 45°C a transparent recording material was obtained.

The recording material was exposed reflectographically to infrared radiation, the second coating being held in direct contact with the infrared-absorbing image markings of a graphic original.

A green image corresponding to those markings was formed.

We claim:

1. A transfer sheet suitable for marking coloured images by a process involving heat-induced transfer of a compound with acid reaction to a receptor sheet incorporating a dye precursor compound, said transfer sheet incorporating as compound with acid reaction a compound corresponding to the following general formula:

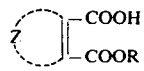

wherein:

Z represents the necessary atoms to close an unsubstituted benzene nucleus, a halogen-substituted benzene nucleus or a nitro-substituted benzene nucleus, and R represents an unsubstituted aliphatic group containing at least 4 carbon atoms, cycloaliphatic group or an aliphatic group substituted with hydroxyl, with an etherified hydroxyl group or with an acyloxy group.

2. A transfer sheet according to claim 1, wherein Z represents the necessary atoms to close a chlorine-substituted benzene nucleus.

3. A transfer sheet according to claim 1, wherein R represents an alkyl group of at least 4 carbon atoms and substituted with hydroxyl.

4. A transfer sheet according to claim 1, wherein said sheet contains the compound with acid reaction in an amount of at least 0.1 g per sq.m.

5. A transfer sheet according to claim 1, wherein the compound with acid reaction is applied in ethylcellulose.

6. A mono-sheet thermosensitive recording material containing a dye precursor compound and a compound with acid reaction, in which material the compound with acid reaction and the dry precursor compound at a temperature below 60°C are kept out of direct chemical contact and the compound with acid reaction corresponds to the following general formula:

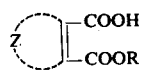

wherein:

Z represents the necessary atoms to close an unsubstituted benzene nucleus, a halogen-substituted benzene nucleus or a nitro-substituted benzene nucleus, and R represents an unsubstituted aliphatic group containing at least 4 carbon atoms, a cycloaliphatic group or an aliphatic group substituted with hydroxyl, with an etherified hydroxyl group or with an acyloxy group.

7. A mono-sheet thermosensitive recording material according to claim 6, wherein Z represents the necessary atoms to close a chlorine-substituted benzene nucleus.

8. A mono-sheet thermosensitive recording material according to claim 6, wherein R represents an alkyl group of at least 4 carbon atoms substituted with an hydroxyl group.

9. A mono-sheet thermosensitive recording material according to claim 6, wherein the dye precursor compound and the compound with acid reaction are kept out of chemical reactive contact below 60°C in separate binder layers.

10. A mono-sheet thermosensitive recording material according to claim 9, wherein one of the binder layers is a top layer that has been applied from a solution in a volatile liquid, which is a non-solvent for the binder of the subjacent other layer.

11. A mono-sheet thermosensitive recording material according to claim 6, wherein the recording material is a clear transparent heat-sensitive sheet material useful in the preparation of a colour projection transparency by thermographic copying procedures and includes a first layer containing the dye precursor compound in a vinyl chloride polymer binder and a second coating bonded to said first layer containing the compound with acid reaction in a binder mainly containing cellulose nitrate.

12. A mono-sheet thermosensitive recording material according to claim 11, wherein the second layer contains as sole binding agent cellulose nitrate and a plasticizer for cellulose nitrate.

13. A mono-sheet thermosensitive recording material according to claim 12, wherein the plasticizer is polyvinyl butyral, a polyalkylene glycol or camphor.

14. A mono-sheet thermosensitive recording material according to claim 6, wherein the dye precursor compound in its binder layer is used in the ratio of 1 part by weight to about 20 to 3 parts by weight of binder.

15. A mono-sheet thermosensitive recording material according to claim 6, wherein the compound with acid reaction is present in its binder layer in a ratio from about 0.1 to about 0.8 parts by weight to 1 part by weight of binder.

16. A mono-sheet thermosensitive recording material according to claim 6, wherein said material comprises a transparent resin support.

* * * * *

UNITED STATES PATENT AND TRADEMARK OFFICE
CERTIFICATE OF CORRECTION

PATENT NO. : 3,965,282
DATED : June 22, 1976
INVENTOR(S) : Wilhelmus Janssens et al It is certified that error appears in the above-identified patent and that said Letters Patent are hereby corrected as shown below:

Column 17, line 52 (Claim 1, line 1), "marking" should read -- making --.

Signed and Sealed this

Seventh Day of September 1976

[SEAL]

Attest:

RUTH C. MASON
Attesting Officer

C. MARSHALL DANN
Commissioner of Patents and Trademarks